(12) United States Patent
Wang

(10) Patent No.: US 8,545,222 B2
(45) Date of Patent: Oct. 1, 2013

(54) METHOD OF DENTAL IMPLANT RESTORATION

(76) Inventor: Chan Qian Wang, Beachwood, OH (US)

( * ) Notice: Subject to any disclaimer, the term of this patent is extended or adjusted under 35 U.S.C. 154(b) by 505 days.

(21) Appl. No.: 12/255,471

(22) Filed: Oct. 21, 2008

(65) Prior Publication Data

US 2010/0099058 A1    Apr. 22, 2010

(51) Int. Cl.
*A61C 8/00* (2006.01)

(52) U.S. Cl.
USPC .......................................................... 433/173

(58) Field of Classification Search
USPC ............... 433/172–176, 218, 219, 220, 221, 433/226, 228.1, 180, 181, 183
See application file for complete search history.

(56) References Cited

U.S. PATENT DOCUMENTS

| | | | | |
|---|---|---|---|---|
| 4,571,181 A | * | 2/1986 | Berger | 433/72 |
| 4,975,059 A | * | 12/1990 | Sendax | 433/173 |
| 5,674,069 A | * | 10/1997 | Osorio | 433/172 |
| 5,762,500 A | * | 6/1998 | Lazarof | 433/213 |
| 6,299,449 B1 | * | 10/2001 | Carlson | 433/180 |
| 2003/0211445 A1 | * | 11/2003 | Klardie et al. | 433/173 |
| 2004/0234926 A1 | * | 11/2004 | Halldin et al. | 433/173 |
| 2005/0084821 A1 | * | 4/2005 | Sims et al. | 433/173 |
| 2006/0019219 A1 | * | 1/2006 | Saliger et al. | 433/173 |
| 2006/0199152 A1 | * | 9/2006 | Hurson et al. | 433/173 |
| 2006/0204928 A1 | * | 9/2006 | Hurson | 433/173 |
| 2008/0124677 A1 | | 5/2008 | Ertl | |
| 2008/0241789 A1 | * | 10/2008 | Mundorf | 433/173 |
| 2008/0274440 A1 | * | 11/2008 | Smith et al. | 433/174 |

FOREIGN PATENT DOCUMENTS

| | | | |
|---|---|---|---|
| DE | 102007026325 A1 | * | 10/2008 |
| GB | 2439926 A | * | 1/2008 |
| JP | 05-253248 | | 10/1993 |
| KR | 10-2007-0054723 | | 5/2007 |

OTHER PUBLICATIONS

International Search Report, International Application No. PCT/US2010/000866, dated as mailed on Jan. 24, 2011, 3 pages in its entirety.

* cited by examiner

*Primary Examiner* — Cris L Rodriguez
*Assistant Examiner* — Mirayda A Aponte

(57) ABSTRACT

The invention provides a method for dental restoration including direct modification of an abutment in the oral environment to obtain the ideal shape, contour, and margin placement. The method is featured with directly measuring the shortest distance X1 between a location L1 on the surface of the abutment and the surface of a surrounding object, and increasing the shortest distance X1 until it is not less than a predetermined value. The invention exhibits numerous merits such as simplified procedure, cost-effectiveness, reduction of laboratory adjustment, reduction of chair time, and reduction of office visits.

6 Claims, 5 Drawing Sheets

METHOD OF DENTAL IMPLANT RESTORATION

BACKGROUND OF THE INVENTION

The present exemplary embodiment relates to a method for dental restoration. It finds particular application in conjunction with the direct intra-oral modification of the abutment component in a sub-crown member, and will be described with particular reference thereto.

The central pulp inside a human tooth is surrounded by a calcareous substance known as dentin, and the pulp communicates with arteries, veins, and nerves. The tooth projects from sockets or alveoli dentalis which are depressions in the alveolar bone of the maxillae (upper jaw) or mandible (lower jaw). The portion of the tooth that actually fits into the socket is formed into one or more roots. The projecting portion of the tooth (known as the crown) comprises grinding surfaces and is covered by a calcified connective tissue known as enamel. Gum or gingival tissue covers the base of the crown and project between adjacent surfaces of teeth; and anchors teeth in place.

Tooth loss may be caused by various diseases such as dental caries, tooth defects, pulpitis, physical injuries, gum disease, and periodontal diseases. Periodontal disease is caused by a sticky film of bacteria called plaque, which over time hardens into calculus. Mild inflammation such as gingivitis may have symptoms of red, swollen and bleeding gums, which may spread to other supporting structures including alveolar bone, producing a more advanced stage of periodontal disease known as periodontitis. The gums recede or pull away from the teeth, resulting in the formation of pockets between the teeth and gums. As the disease progresses, teeth become loose, often necessitating extraction. Thus, periodontal disease is a major cause of tooth loss.

In prior arts, there have been a variety of methods devised to implant and secure a dental prosthesis. The most common type of implant is endosseous, in which an implant is first surgically placed into the patient's jawbone. The implant serves to mimic a root structure and protrudes through the gum to hold an abutment adapted to receive a dental prosthesis. A common abutment is a substantially cylindrical device that is typically screwed into the implant, and the crown is then affixed on top of the abutment. A traditional way known to a skilled dentist in dental restoration of implant includes the following 12 steps: (1) take off the sealing cap; (2) prepare the tray, and try the impression tray on, drawing the line to cut and open the window to allow the impression coping to stick out (known as open-tray technology); (3) put regular impression coping on, and screw tight; (4) put impression material into the prepared tray; (5) press the impression on top of the impression coping, and wait until set; (6) unscrew the impression coping; (7) place wax to close the open window around the portion sticking out of the impression coping; (8) take off the impression tray with impression coping on it; (9) connect the implant analog with the impression coping and send all together to dental lab; (10) A laboratory technician will pour material and prepare a stone model, then send it back to the dentist; (11) the dentist chooses the abutment he or she thinks will fit the stone model best, and will send it back to the laboratory; and (12) the laboratory technician adjusts the abutment, then may send it back the dentist to try on the patient's mouth, then re-adjusts the abutment again based on the dentist's prescription, and makes the crown on top of the abutment.

However, current restoration processes are disadvantageous in that they are procedurally very complicated, causing low penetration rate for dental implants. Now less than 5% general dentist can do surgical placement of dental implant, and less than 10% of general dentist actually do implant restoration due to the complications of the current technology. To increase the penetration rate of the implant in restoration dentistry, a dentist needs to use a simplified restoration procedure and technology, which should be straightforward, cost effective, and include a minimal number of office visits. The need is also highlighted by the burden that in order to properly transfer an accurate model of the soft tissue in the area of the planned implant, most abutment systems now use closed tray or open tray impression technologies. These require a modification of the abutment in the lab by a dental lab technician; or in an alternate approach, a doctor uses a temporary plastic abutment, modifies it in the patient mouth, then sends it to a lab to cast the metal abutment base on the shaped temporary abutment. Such complicated procedures significantly increase the lab fees, reduce dentist's profit from ¼ to ⅓, and/or costs the patient more in fees and time.

Another problem is that dental implant systems in prior art require a vast array of threaded coronal prosthetic attachments to accommodate different restoration methods utilized in the dental practice. Currently, there are three primary restoration methods, a fixed single or multiple unit cementable crown prosthesis, a removable single or multiple unit screw retained prosthesis or a removable overdenture prosthesis. In order to accommodate these different restoration methods, a vast inventory of different components are needed, requiring a significant investment in time and money by dental professionals.

Still another problem associated with dental implants is the inability to select the final abutment by the surgeon and restorative dentists. The dental laboratory typically decides what the configuration of the abutment will be by analyzing the plaster impressions taken of the patient's mouth. This prevents the surgeon or restorative dentist from being able to observe and possibly correct any angle problem or tissue height discrepancy.

Advantageously, the present invention provides a new method for dental implant restoration, which exhibits numerous merits such as simplified procedure, cost-effectiveness, reduction of chair time, elimination of 1-2 lab trips, and reduction of office visits. In some embodiments, the present invention enables an oral surgeon or restorative dentist to modify the abutment at any time so as to allow for the ideal shape, contour, and margin placement. The method of the invention can be completed in the dentist's office with minimal to no margin existing between the gum tissue and the crown once it is installed, and eliminate the need of sending the abutment system back to the dental laboratory for adjustment.

BRIEF DESCRIPTION OF THE INVENTION

The present invention provides a method for dental restoration in an oral environment comprising:

(i) placing a sub-crown member comprising an abutment component and a dental implant component into a jawbone;

(ii) directly measuring the shortest distance $X_1$ between a location $L_1$ on the surface of said abutment component and the surface of an object surrounding said abutment component in the oral environment;

(iii) comparing value $X_1$ with a predetermined value $Y_1$, wherein $Y_1 > 0$;

(iv) if $X_1 < Y_1$, directly modifying the abutment component on its location $L_1$ in the oral environment to increase said shortest distance $X_1$ until $X_1 \geq Y_1$; and (v) optionally repeating steps (ii)-(iv) on one or more of other locations Ln on the surface of said abutment component with corresponding shortest distances Xn and corresponding predetermined values Yn, wherein Yn>0, n is an integer, and n≥2.

BRIEF DESCRIPTION OF THE DRAWING

FIG. 2a shows a sub-crown member comprising an abutment component 201 and a dental implant component 202 which is placed into a jawbone 299. The shortest distance X1 between a location L1 203 on the surface of said abutment component 201 and the surface of an object such as an upper tooth 204 surrounding said abutment component 201 in the oral environment is directly measured. Value X1 is compared with a predetermined value Y1 (wherein Y1>0).

FIG. 2b shows that the abutment component 201 is directly modified with a tool such as a bur 210 on its location L1 203 in the oral environment, if it is found that X1<Y1 in FIG. 2a.

FIG. 2c shows that the shortest distance X1 is increased until X1≥Y1 after the abutment component 201 is directly modified in FIG. 2b.

FIG. 2d shows that the above procedure as shown in FIG. 2a—FIG. 2c can be optionally repeated likewise on one or more of other locations Ln 215 on the surface of said abutment component 201 with corresponding shortest distance Xn from the surface of an object such as a neighbor tooth 214 surrounding said abutment component 201 in the oral environment. In FIG. 2d, the corresponding predetermined value is Yn, wherein Yn>0, n is an integer, and n≥2.

DETAILED DESCRIPTION OF THE INVENTION

Figure 1:
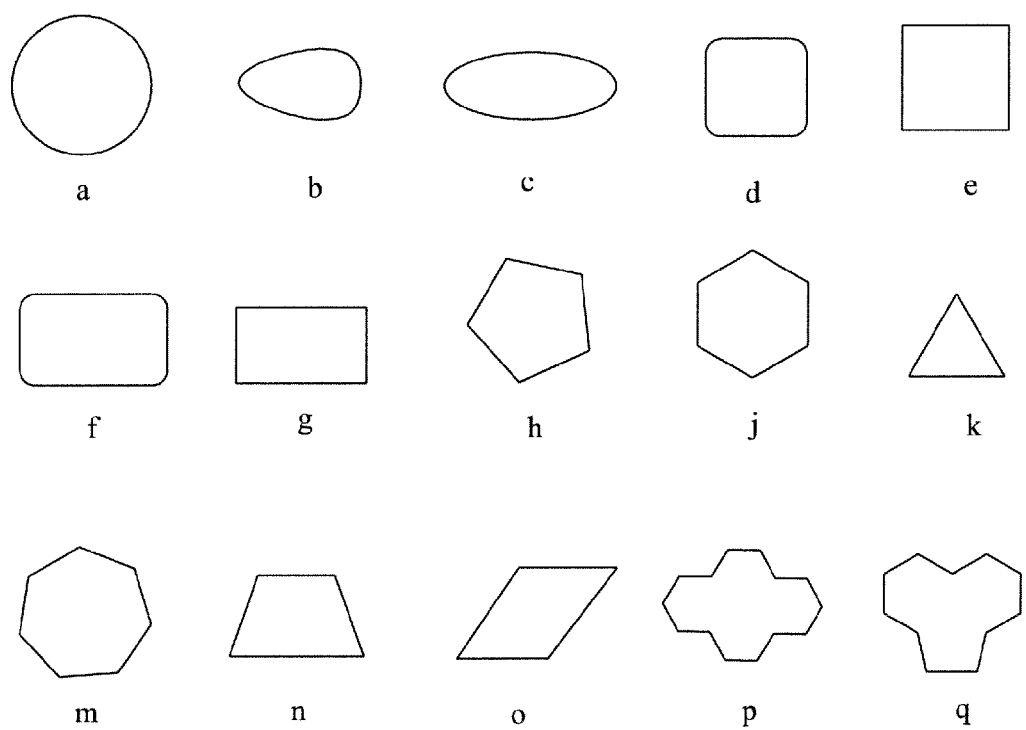
FIG. 1 illustrates a part of designed cross-sectional shapes of the abutment component in a sub-crown member according to an embodiment of the invention. However, the shapes are not imitative to the invention, and other regular and irregular cross-sectional shapes are contemplated to be within the scope of the invention as well.
Figure 2A:
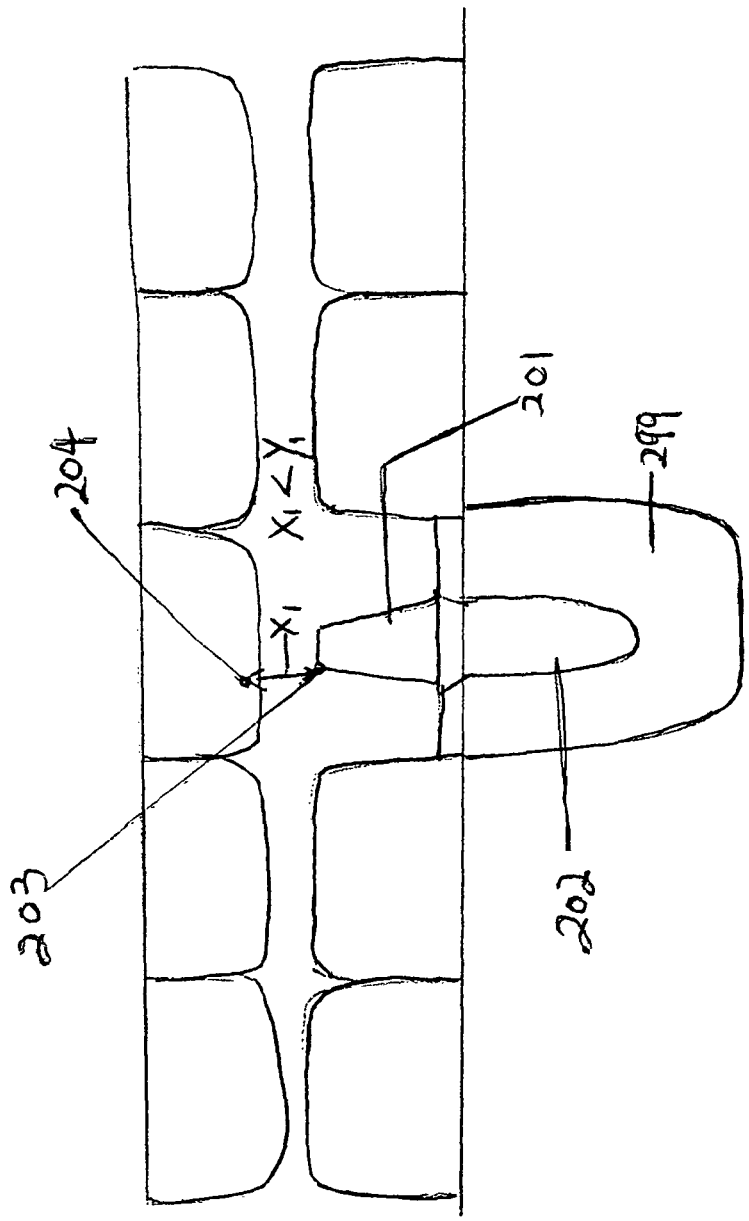
FIG. 2a, FIG. 2b, FIG. 2c and FIG. 2d illustrate a method of dental restoration in an oral environment according to an embodiment of the invention.
Figure 2B:
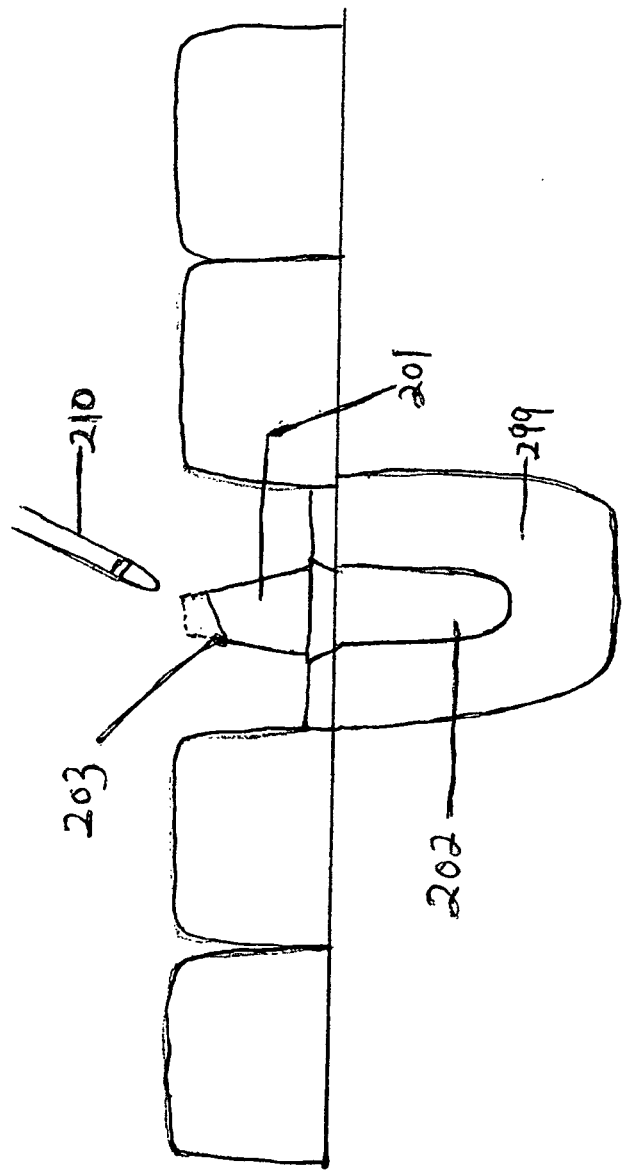
Figure 2C:
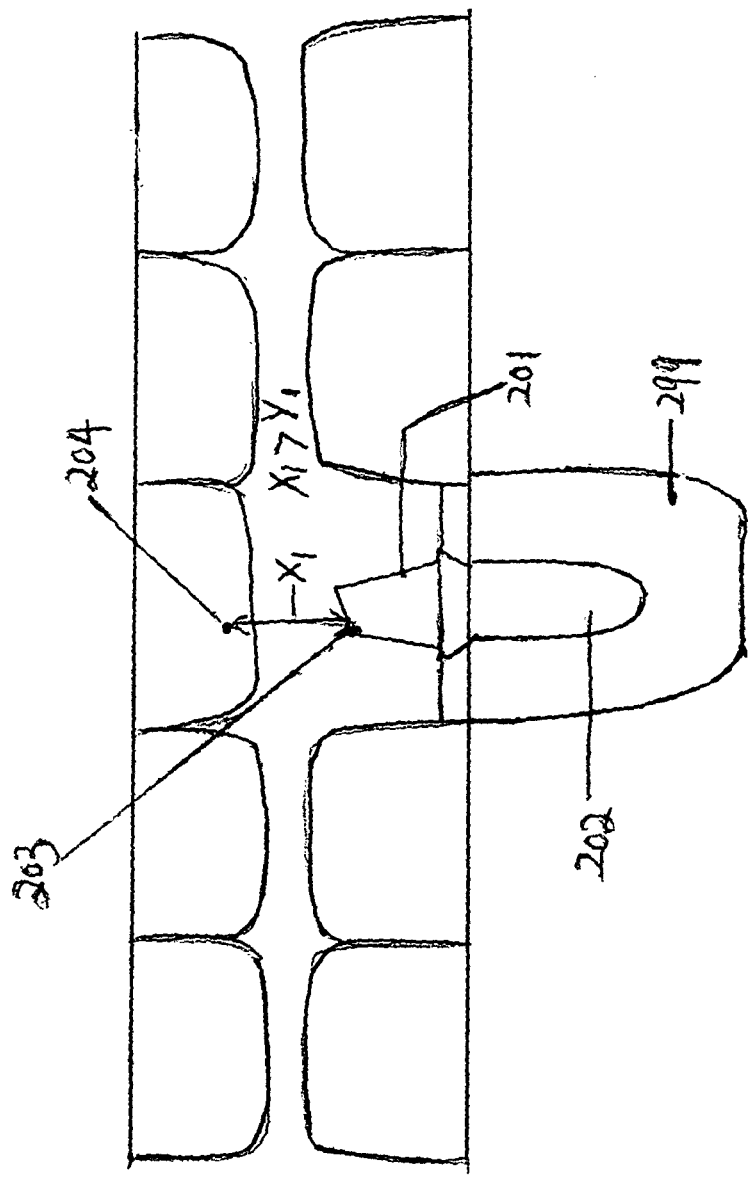
Figure 2D:
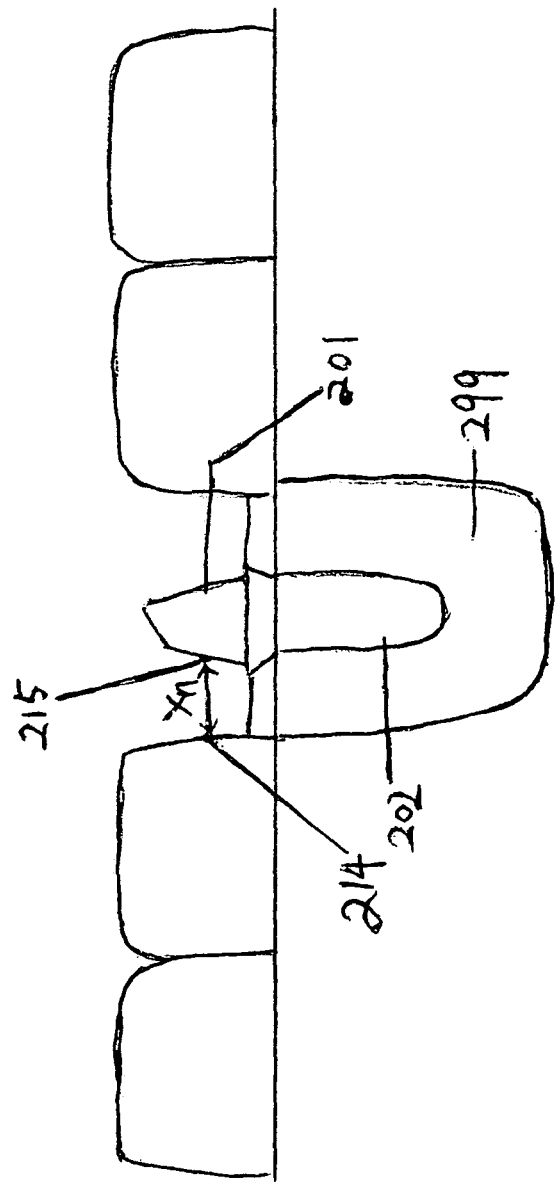

The present invention can be employed in the replacement of either a single tooth or of multiple teeth. In the replacement of a single tooth, the site may be first prepared by conventional techniques. Preparation of the site may involve drilling a hole that is the approximate width of the dental implant component in the sub-crown member. Alternatively, the site may be prepared by tapping a hole of the proper size and thread dimensions such that a threaded dental implant component in the sub-crown member can threaded into the hole and retained by the surrounding tissue. Multiple teeth are commonly replaced using implants and implant bridgework. For example, a prosthesis covering a gap caused by multiple missing teeth can be anchored at one end by a modifiable abutment component in the sub-crown member according to the present invention and at another end by adhesion to a prepared natural tooth (or a dental implant sub-crown member). The prosthesis anchored at both ends serves as a "bridge" over the gap.

There is no specific limitation on the physical and chemical relationship between the abutment component and the dental implant component in the sub-crown member. For example, they may be two separate components and are connected and secured to each other to form a two-piece sub-crown member using known techniques. Alternatively, they can be integrated into a one-piece sub-crown member, each using different or same materials.

In some embodiments of the invention, a two-piece sub-crown member may be preferred because the dental implant component can not bear normal mastication forces upon initial installment. Only after the supportive tissue had grown around the implant could the abutment component and prosthesis such as the crown be installed. In the intervening period, a closure screw may be inserted into the implant to keep the interior of the implant clean and prevent contamination of the surrounding tissue. Moreover, various cuff height, contour, and angles of the abutment component may be selected to closely replicate the desired height, angles, and profiles needed in the oral environment. In this manner, the amount of modifications and alterations to the abutment component, although remain, may be minimized, so that, in step (v) of the invention, steps (ii)-(iv) may be repeated for few or even zero times.

For a two-piece sub-crown member, the implant is adapted to mate with the abutment. In an embodiment, the implant has internal threads, external threads, and/or other designs that serve to receive the abutment. The implant component and the abutment component can be connected using screws, cement, or other techniques known to those skilled in the art. For a one-piece sub-crown member, the implant component may be tapered at the top to form an abutment such that the top of the implant can receive the crown.

In preferred embodiments of the invention, the dental implant component in the sub-crown member is rigid, bio-compatible, and ankylosing. The material of the dental implant component preferably permits and encourages osseointegration or osteo in-growth (growth of bony tissue), also known as ankylosis, into the dental implant component. For example, the implant component may have a hollow or solid structure. A hollow structure will encourage osteo in-growth into the implant component. Alternatively, the implant component may contain holes penetrating the wall of the implant to further promote osteo in-growth. The bottom section of the implant component may be tapered in order to provide dynamic loading on the surrounding bone and tissue along the entire length. For example, the bottom taper may be approximately between about 2 to about 3 degrees. The bottom section of the implant tapers from top to bottom, that is, the diameter of the implant component decreases from top to bottom.

In various exemplary embodiments of the invention, the dental implant component may comprise a material selected from the group consisting of pure titanium, titanium oxide (TiO), titanium alloy such as $TiAl_6V_4$ alloy, stainless steel, zirconium, cobalt-chromium-molybdenum alloy, polymeric material, and any combination thereof.

In some exemplary embodiments of the invention, the dental implant component comprises a polymeric material which is bio-stable, and a pharmaceutical agent may be incorporated in the polymeric material. The pharmaceutical agent may diffuse out of the polymeric material to surrounding tissues such as the bone tissue and nearby tissue. In other words, the pharmaceutical agent may be delivered either locally or systematically by the polymeric material in the implant component. Examples of pharmaceutical agent include, but are not limited to, steroidal anti-inflammatory agents, biocides, antiviral compounds such as acyclovir and interferon; antiprotozoals such as chloramphenicol, and sulfamethoxazole; analgesics; steroidal analgesics such as aspirin, salicylic acid, diflunisal, morphine and its salts; antiseptic substances such as cetylpyridinium chloride, benzalkonium chloride, chlorhexidine and the like; antimycotic substances such as cetyltrimethylammonium bromide, antifungals such as polyoxyethylene nonylphenols, alkylaryl sulfonates, miconazole nitrate, metronidazole, and trimethoprim; local anesthetics such as salts of procaine, benzocaine, lidocaine, procaine, bupivacaine, tetracaine, xylocalne, mepivacaine and their salts; antiasthma drugs such as adrenaline, ephedrine, epinephrine, aminophylline, and theophylline; anticoagulants such as heparin and its salts such as calcium and sodium heparin, and bishydroxycoumarin; antihypertensive substances such as methyldopa, hydralazine, clonidine, chlorothiazide, timolol, propanolol, metoprolol, prazosin hydrochloride, and furosemide; and vitamins such as B6, B12 and C. Steroidal anti-inflammatory agents may be selected from corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chloroprednisone acetate, clocortolone, clescinolone, dichlorisone, difluprednate, flucioronide, flunisolide, fluorometholone, fluperolone, flupredniso- lone, hydrocortisone valerate, hydrocortisone cyclopentylpropionate, hydrocortamate, meprednisone, paramethasone, prednisolone, prednisone, beclomethasone dipropionate, triamcinolone, and mixtures thereof. The preferred steroidal anti-inflammatory for use is hydrocortisone.

In various embodiments, the abutment component in the sub-crown member is pre-manufactured and comprises a material that is rigid, bio-compatible, and optically similar to dentin.

In various embodiments of the invention, the abutment component may have pre-manufactured lengths and pre-manufactured angles, although such pre-manufactured or pre-contoured abutment components are not yet able to be adapted to all patients in all cases. For example, the abutment component of the present invention may be pre-prepared in any desired shape or size, including cylinders, bars, cubes, polyhedra, ovoids, and plates. FIG. 1 illustrates some exemplary cross-sectional shapes of the abutment component according to the present invention, however with variable size and center at different heights.

In an embodiment, the abutment for front teeth can be flat abutment specially designed for anterior tooth, which fit the nature anatomy structure MD distance (> facial-lingual distance).

Generally, the pre-manufactured abutments, even with near-exact shape and morphology, still need to be subjected to further modifying and shaping processes to create the desired product that fits the specific oral environment of a patient.

After a pre-prepared abutment component has been successfully modified to fit a patient's oral environment, it not only can secure the crown to the sub-crown member, it can also compensate for a misalignment, if any, between the prosthesis and adjacent teeth. Misalignment can arise, for example, when the implant component has an orientation with respect to the gum surface that is substantially different than the adjacent teeth. As such, the present invention may eliminate the need for angled abutments in the prior art to account for any misalignment.

The pre-manufactured abutment components of the invention are preferably manufactured in an industrial scale, and supplied as ready-to-modify commercial products. However, they can also be custom made in a conventional manner, for example, by modeling. As known to a skilled person, a mold may be produced from a wax model. The wax is then melted in a furnace to produce a negative mold, which is then melted out with suitable material such as alloy.

In preferred embodiments, the material used to make the abutment component in the present invention, alone or in combination with the material used to make the crown, with or without a coating thereon, can exhibit appealing optical properties and thus high aesthetic value, such as color, shade, transparency, and translucence, which imitate the appearance of the natural teeth. For instance, the abutment component may have a visible area near the gums that is not covered by a crown. When these visible areas are directly made of metals or plastics that do not have the color of natural teeth, the dental devices provide a non-esthetically pleasing appearance on the patient's face.

Although any modifiable material may be used in the invention, merely in terms of aesthetic value, the present invention prefers porcelains, composites and ceramics to amalgam and metals, since they better matches with the color of adjacent natural teeth.

Transparency of a human tooth is gradually decreased from enamel to dentin. As such, in preferred embodiments of the invention, a material having high transparency is used for the crown, while a material having low transparency and chroma is used for the abutment component.

When necessary, one or more coloring agents may be mixed and formulated, and then used as or in the material of the abutment component and the crown, giving a color tone similar to that of dentin and enamel. For example, a pink coloring agent may be obtained by dissolving manganese oxide in aluminum oxide as a solid solution. A yellow coloring agent may be obtained by dissolving vanadium oxide in zirconium oxide as a solid solution. Examples of coloring agent include, but are not limited to, oxides of Pr, Er, Fe, Co, Ni, Ti, V, Cr, Cu and Mn, such as $Fe_2O_3$, $Er_2O_3$, and $MnO_2$. In a specific embodiment, a mixture of $Er_2O_3$, $Pr_6O_{11}$, $Fe_2O_3$, ZnO, and zirconium oxide gives a dentin color.

For some other patients, the physical, and chemical, and biological properties of the material may have a higher priority than the aesthetic value. In this case, the present invention preferably selects materials that have high strength, performance, bio-compatibility and chemical durability so that they can take over the function of the natural tooth material and maintain these properties over a sufficient period of time while being permanently in contact with fluids in the oral cavity which can even be aggressive, such as acidic in nature. The abutment material of the invention may have a broad range of these properties, as long as it remains a modifiable material that serves the purpose of the invention. For example, an exemplary parameter to characterize the abutment material is hardness H in the unit of K.H.N. (Knoop Hardness Number) under the ASTM D-1474 standard. Despite that dentin may have a narrow hardness range such as 30-70 K.H.N., the material used in making the abutment component can be generally equal to or greater than 10 K.H.N., preferably equal to or greater than 30 K.H.N., and more preferably equal to or greater than 70 K.H.N.

In the Knoop hardness test, a pyramidal diamond point is pressed into the polished surface of the test material with a known force, for a specified dwell time, and the resulting indentation is measured using a microscope. The Knoop hardness HK or KHN is then given by the formula: HK=Load (kgf)/impression area (mm$^2$)=P/($C_p L^2$), where L=length of indentation along its long axis, Cp=correction factor related to the shape of the indenter, ideally 0.070279, and P=load. However, it should be understood that there are other ways to characterize the hardness and strength of a material than the Knoop Hardness Number, which are all perceived as within the scope of the present invention. For example, Mohs hardness scale characterizes the scratch resistance of various minerals through the ability of a harder material to scratch a softer material. In a specific embodiment, the abutment component of the invention has a Mohs hardness of from about 2.0 to about 5.8. In another specific embodiment, the abutment component of the invention has a Mohs hardness of from about 6.2 to about 9.8.

In some embodiments of the invention, the abutment material may be so preferably selected that, when it is subject to the direct modification right in the oral environment of a patient, it can be modified, shaped, re-modified, and re-shaped in an easy manner within a short time, without undue wear of the modifying tools, and without any healthy risks.

In preferred embodiments, the direct modification of the abutment component does not have any undesirable effect, such as heat shock, against the jawbone. For example, the modification is so controlled that only a limited amount of heat is produced; the abutment and implant materials have lower thermal conduction and does not transfer the heat to the jawbone; and, if necessary, a cooling system may be used to control the heat and to protect the jawbone. In an especially preferred embodiment, a non-titanium material is used to prepare the abutment component.

In preferred embodiments, the abutment component can go through the modification process without micro-fracture, in addition to that it is biocompatible, not degradable in an oral environment, strong enough to support the crown for mastication faction, and also meet the aesthetic requirement.

A step of the present invention is directly measuring the shortest distance X1 between a location L1 on the surface of the abutment component and the surface of an object surrounding the abutment component in the oral environment, which may be, for example, a periodontal tissue, a gum tissue, a tooth, prosthesis, and any combination thereof. The shortest distance X1 is estimated to be similar to or same as the maximal thickness of the crown in location L1. As known to a skilled dentist, there are some strict or preferred thickness requirements for a crown, to make the finally restored "tooth" fit in the oral environment, and function well too. For example, the thickness of a crown on top of the abutment component may range from 1 mm to 3 mm for sake of chewing strength, while the thickness around the abutment component may range from 0.01 mm to 0.5 mm. Various thickness requirements enable a dentist or a computer to determine the predetermined value Y1 (and Yn if necessary) on specific location L1 (and Ln if necessary).

If X1<Y1, the thickness of the crown on that location L1 would fail to meet the thickness requirement on that location. According to the invention, the abutment component is directly modified or shaped in the oral environment (without removing it from the mouth) on the very location L1 to increase the shortest distance X1 until X1≥Y1, in other words, to meet the thickness requirement on location L1.

The location L1 and Ln should be understood broadly to include not only a point, but also a small area such as 0.5 mm$^2$, 1.0 mm$^2$, 2.0 mm$^2$, and so on, on the surface of the abutment component that need to be directly modified.

There may be one, two or more locations on the surface of the abutment component that need to be directly modified, for example, a dentist may need to directly modify 3 locations L1, L2, and L3 around the abutment component, and 2 locations L4 and L5 on top of the abutment component, each with corresponding shortest distances X1, X2, X3, X4, and X5; and corresponding predetermined values Y1, Y2, Y3, Y4, and Y5.

In various embodiments, the direct modifying of the abutment component may be performed by a mechanical means, a chemical means, an optical means such as laser cutting and UV-degradation, a thermal means such as controlled heating, and any combination thereof. Various actions in the modification include, but are not limited to, cutting, carving, cross cutting, milling, grinding, trimming, adjusting, finishing, abrading, polishing, controlled vaporization, removing, shaping, electronic discharge milling (EDM), and cutting by water jet or laser. For example, the direct modification may utilize a tool (e.g. hand-held tool) known to a skilled dentist, such as a bur or a rotary file; diamonds; multi-use diamond dental bur; a dental carbide bur made of e.g. tungsten carbide steel; a dental sintered diamond bur; conical milling burs; a dental diamond disc; a tungsten carbide cutter; parallel milling cutter; dental steel bur, and the like, and any combinations thereof. A bur blade may be in the form of (or for the purpose of) round, wheel, inverted cone, straight fissure, taper fissure, amalgam prep, pear shape, flame, cone, egg, taper, bullet, needle, straight fissure crosscut, taper fissure crosscut, end cutting, straight dome, straight dome crosscut, and taper dome. For example, carbide cutters (standard) may be used for adjusting acrylic, stone and plaster; carbide cutters (coarse) for rapid, smooth adjustments on acrylic, stone and plaster; and carbide cutters (extra fine) for smoothing metal, porcelain and temporary acrylic. Lab carbide cutters (fine) crosscut may be used for smooth trimming on metal, acrylic, and stone; for rapid cutting on all metal, acrylic, and stone; and for rapid reduction on acrylic and plaster. During the modification, the contact area may be dry, or it may be flushed with or immersed in a lubricant. Alternatively, it may be flushed with an air or gas stream. Suitable liquid lubricants are well known, and include water, oils, glycerine, ethylene glycols, and silicones.

In the direct modification of the abutment component, the invention may also utilize computer automated equipment, frequently referred to as "digital dentistry", where computer automation is combined with optics, digitizing equipment, CAD/CAM (computer-aided design/computer aided machining) and mechanical tools.

In preferred embodiments, particularly when the strength of the abutment component is very strong, it may be chemically pretreated before the modification with other means such as mechanical means, to weaken its strength (or soften) on location L1 (and Ln if necessary) and make the modification easier. The chemical pretreatment may be selected from salvation or dissolution with a solvent, vaporization, a chemical reaction such as etching and degradation using reagents such as HF, a base, an acid, and a complexing agent.

In various embodiments, the abutment component comprises a material selected from the group consisting of metals; oxides; carbides such as silicon carbide; borides; nitrides; silicides; salts such as aluminosilicates, silicates such as lithium silicate, aluminates, phosphates, fluorates, zirconates, and titanates; ceramic materials such as a porcelain, a white stone containing alumina, and a glass; polymeric materials; any composites thereof such as inorganic-inorganic composites optionally bound by an organic binder, and polymeric-inorganic composites; and any combination thereof.

In general embodiments, the abutment component material may be an inorganic-inorganic composite optionally bound by an organic binder, or an organic material such as a polymeric material including various optional inorganic/organic ingredients for functional and aesthetic purposes.

A ceramic material of the invention is defined as a material having a glazed or unglazed body of crystalline or partly crystalline structure, or of glass, which body is produced from essentially inorganic, non-metallic substances and either is formed from a molten mass which solidifies on cooling, or is formed and simultaneously or subsequently matured by the action of the heat. For example, technical ceramics can be classified into three categories: (1) oxides such as alumina and zirconia; (2) non-oxides such as carbides, borides, nitrides, silicides; and (3) composites such as particulate reinforced, combinations of oxides and non-oxides.

Porcelain of the invention is a ceramic material made by heating raw materials, generally including clay in the form of kaolin, in a kiln to temperatures between 1,200° C. and 1,400° C. The toughness, strength, and translucence of porcelain arise mainly from the formation of glass and the mineral mullite within the fired body at these high temperatures. Glass of the invention is an inorganic product of fusion which has been cooled to a rigid condition without crystallizing. Many glasses contain silica ($SiO_2$) as their main component. The glass of the invention may be extended to all amorphous solids, including plastics, resins, or other silica-free amorphous solids.

In a preferred embodiment, aluminum oxide is used in the abutment material since it is strong, hard, colorless, and readily available. It is preferred that the average grain size of the ceramic material be no greater than 1.0 micrometer (micron).

In various embodiments of the invention, the abutment component comprises one or more metals selected from the group consisting of titanium, stainless steel, gold, silver, platinum, iron, palladium, iridium, osmium, rhodium, ruthenium, an amalgam, any alloy thereof, and any combination thereof. For example, an abutment component may be made of an alloy comprising from 35 to 50 weight percent gold, 15 to 50 weight percent platinum, 15 to 50 weight percent palladium, and 0.1 to 5.0 weight percent iridium. Amalgam is a commonly used dental filling, and it is a mixture of mercury with at least one other metal. For example, a dental amalgam may comprise by weight 43-54% mercury, 20-35% silver, 10% copper, 2% zinc, and tin.

Examples of oxide used in the invention include, but are not limited to, oxides of the elements in groups IIIa, IIIb and IVb in the periodic table; oxides of Hf, Y, Ce, Sc and Er; zirconia, aluminous oxide or alumina, silica, SIALON, mullite, $Li_2O$, $ZnO$, $K_2O$, $P_2O_5$, $CaO$, $BaO$, $SrO$, and $MgO$; coloring and fluorescent metal oxides such as $Tb_4O_7$, $Ta_2O_5$, $Er_2O_3$, $Pr_2O_3$, $La_2O_3$, $Y_2O_3$, $CeO_2$, $MnO_2$, $Fe_2O_3$, and $V_2O_5$; any composite thereof, and any combination thereof.

Examples of polymeric material used in the invention include, but are not limited to, a thermoset material, a thermoplastic material, an acrylic polymer, a methacrylic polymer, poly(methyl methacrylate) (PMMA), polyethyl methacrylate), poly(butyl methacrylate), polyamides, polyesters, a polyaryl ether ketone (PAEK), polyether Ketone Ketone (PEKK), polyether ether ketone (PEEK), polyether ketone ether ketone ketone (PEKEKK), a vinyl ester, an epoxy resin, a polyimide, a polyarylate, a polyacrylate, a photosensitive polymer, a polyolefin, an ultra high molecular weight polyethylene, a high density polyethylene (HDPE), a polyurethane, a polypropylene, a polystyrene, an acrylated polyester, a styrene acrylonitrile copolymer, a ABS polymer, a polysulfone, a polyacetal, a polycarbonate, polyurethane dimethacrylates (PUDMA), triethylene glycol dimethacrylate (TEGDMA), polyethylene glycol dimethacrylate (PEGDMA), urethane dimethacrylate (UDMA), a polymer of 2-hydroxyethyl methacrylate (HEMA), ethylene glycol dimethacrylate (EGDMA), diethyleneglycol dimethacrylate (DEGDMA), triethylene glycol dimethacrylate (TEGDMA), tetrahydrofurftiryl methacrylate, trimethylolpropane trimethacrylate (TMPTMA), diphenyl sulfone dimethacrylate, polytetramethyleneglycol dimethacrylate (PTMGDMA), hexane diol dimethacrylate (1,6 HDDMA), polycarbonate dimethacrylate (PCDMA), a polyphenylene sulfide; a mixture of urethane dimethacrylate (UDMA), polycarbonate dimethacrylate (PCDMA) and triethyleneglycol dimethacrylate (TEGDMA); bis-glycidyl-methacrylate adduct of bisphenol A (Bis-GMA) and its acrylic counterparts; the adducts of 2,2,3-trimethylhexane diisocyanate with hydroxyalkyl acrylic species such as hydroxyethyl methacrylate and hydroxypropyl methacrylate; any copolymer thereof, and any combination thereof.

In various embodiments of the invention, the polymeric materials can be prepared from one or more monomers or oligomers selected from the group consisting of methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, butoxyethyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, ethylene glycol dimethacrylate, diethylene glycol dimethacrylate, triethylene glycol dimethacrylate, triethylene glycol trimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, trimethylolmethane trimethacrylate, pentaerythritol trimethacrylate, pentaerythritol tetramethacrylate, polyoxytetraethylene glycol dimethacrylate, 2,2-bis (methacryloxyphenyl)propane, 2,2-bis(4-(2-hydroxy-3-methacryloxypropoxy)phenyl)propane, 2,2-bis(4-methacryloxydiethoxyphenyl)propane, 2,2-bis(4-methacryloxypoiyethoxyph-enyl)propane and an acrylate thereof, and a methacrylate having a urethane bond in the molecule, such as di-2-methacryloxyethyl-2,2, 4-trimethylhexamethylene dicarbamate, 1,3,5-tris(1,3-bis(methacryloyloxy)-1-2-propoxycarbonylaminohexane)-1,3,5-(1H, 3H, 5H)triazin-2,4,6-trio ne, a urethane oligomer synthesized of 2,2'-di(4-hydroxycyclohexyl)propane, 2-oxepanone, hexamethylene diisocyanate and 2-hydroxyethyl methacrylate, and a urethane oligomer synthesized of 1,3-butanediol, hexamethylene diisocyanate and 2-hydroxyethyl methacrylate.

In making the polymeric material, compounds such as polymerization initiators, polymerization accelerators, ultraviolet light absorbers, and anti-oxidants, and other additives well known in the art may be used. The polymeric material may be visible light curable, self-curing, dual curing, and vacuum, heat, and pressure curable compositions as well as any combination thereof. It may be fully or partially polymerized using photo, chemical or thermal means under controlled pressure or atmospheric pressure. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, a heat cure initiator such as benzoyl peroxide, 1,1'-azobis(cyclohexanecarbo-nitrile), or other free radical initiators.

In self-curing, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like.

A heat cure initiator may include benzoyl peroxide, 1,1'-azobis(cyclohexanecarbonitrile), or other suitable free radical initiators. Particularly suitable free radical initiators are lauroyl peroxide, tributyl hydroperoxide, AIBN and, more particularly benzoyl peroxide or 1,1'-azobis(cyclohexanecarbonitrile).

Various optional ingredients may be used with the polymeric materials, for example, a pigment; an opaque on the exterior surface; fibers, powders, and particulates; a fiber reinforcement such as a glass fiber reinforcement, bariumborosilicate glass flit, glass fiber-reinforced composites (FRC) such as light polymerized glass fiber-reinforced composites; fillers such as silica, silicate glass, quartz, barium silicate, barium sulfate, barium molybdate, barium methacrylate, barium yttrium alkoxy (Ba2Y(OR)X), strontium silicate, barium borosilicate, strontium borosilicate, borosilicate, lithium silicate, amorphous silica, ammoniated or deammoniated calcium phosphate and alumina, zirconia, tin oxide, tantalum oxide, niobium oxide, titania, carbon, graphite, polyaramid, polyethylene, polyesters, and polyamides; and any combination thereof; an inorganic filler containing powder of glass, such as silicon dioxide, barium glass, alumina glass, potassium glass and fluoroaluminosilicate glass, synthetic zeolite, calcium phosphate, feldspar, fumed silica, aluminum silicate, calcium silicate, magnesium carbonate and quartz, wherein the inorganic filler may optionally be subjected to a surface treatment with gamma-methacryloxypropyltrimethoxysilane, vinyltrichlorosilane, vinyltriethoxysilane, vinyltrimethoxysilane, vinyltriacetoxysilane, and vinyltri(methoxyethoxy)silane; and any combination thereof.

The reinforcing component may comprise, to name a few possible examples, at least one selected from the group comprising carbon, Al2O3, ZrO2, Y2O3, Y2O3-stabilized ZrO2, MgO-stabilized ZrO2, E-glass, S-glass, bioactive glasses, bioactive glass ceramics, calcium phosphate, hydroxyapatite, TiO2, Ti, Ti6Al4V, and stainless steel. The geometry of the reinforcing component may include fibers, particulates, variable diameter fibers and fibers fused with particulates on the fiber surfaces.

In one example, the abutment component of the invention may comprise about 55% by weight of the PEKK as the matrix material, about 35% by weight of E-glass fibers as the reinforcing material, and about 10% by weight of titanium dioxide particles as the colorant.

In another example, the abutment component of the invention may comprise zinc oxide, glass fillers containing strontium oxide, zirconium oxide, Bisphenol A-based epoxy resin matrix, and E-glass fibres.

Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania.

The reinforcing fiber element of the polymeric material preferably comprises glass, carbon, graphite, polyaramid, or other fibers known in the art, such as polyesters, polyamides, and other natural and synthetic materials compatible with the polymeric matrix. The fibers may further be treated, for example silanized, to enhance the bond between the fibers and the polymeric matrix. The fibers preferably take the form of long, continuous filaments. Suitable coupling agents include silane compounds such as organo-silane agents. Exemplary silane agents include gamma-methacryloxy propyltrimethoxysilane, gamma-aminopropyl triethoxysilane, vinyl trichlorosilane and styrylamine functional silane.

In preferred embodiments, the crown is directly produced in a dentist office rather in a lab based on the shape of the modified abutment component. However, it should be understood that any known manual and digitalized methods may also be used to make a crown, which are within the scope of the invention.

Since the oral environment such as state of a dental caries and the intra-oral shape vary in patients one by another, a dental prosthesis to be prepared is also different in the patients one by another. Accordingly, the form of the dental prosthesis is designed and prepared taking into account the relation with antagonists or adjacent teeth or the occlusal relation. The completed prosthesis preferably has a high dimensional precision in the order of several μm.

The present invention may employ a digital and automatic procedure such as a CAD/CAM (computer-aided design and manufacturing for using in a dental office and a dental lab) system in which a dental prosthesis such as a crown is designed on a screen utilizing a computer and prepared by milling processing. For example, a CAD/CAM system commercialized in dental offices as the Cerec system (e.g. Cerec 2® and Cerec 3®) from Siemens AG, Germany, is preferably used in the invention. This CAD/CAM system is a process in which the shape of a tooth subjected to preparation of abutment tooth or cavity preparation and if necessary, the shapes of adjacent teeth or antagonists are read out; a desired dental prosthesis is designed based on the read-out tooth shape using a computer; and a block-like material such as a resin cured material, a ceramic sintered material, and a metal material is set in an automatic milling processor and subjected to milling processing to prepare the desired dental prosthesis. The CAD/CAM system is characterized in that dental prostheses can be prepared with good efficiency, and that dental prostheses having superior fitness precision in an oral cavity can be prepared.

The crown may comprise any material selected from porcelain, metal, metal alloy, ceramic material, polymeric material, and any combination thereof. In a preferred embodiment of the present invention, the ceramic material for the crown is a translucent polycrystalline material, because the natural tooth enamel has a high translucency, whereas dentine has a lower translucency. A polycrystalline material has a multiplicity of randomly oriented crystals joined at grain boundaries. Preferably, the ceramic material is substantially nonporous to maintain a high degree of optical translucency. Translucency is the property of a specimen by which it transmits light diffusely without permitting a clear view of objects beyond the specimen and not in contact with it. A translucent material is an advantage because a crown, for example, formed from such a material effectively blends in with its surroundings and assumes the color of the underlying tooth and the teeth adjacent to it. This can provide improved aesthetics as compared to more opaque materials.

In some embodiments, a dentist may need to color-match a prosthesis such as a crown with the color and shade of the dentition that surrounds the prosthesis.

In an embodiment, the ceramic material for the crown is an alpha aluminum oxide. Aluminum oxide is particularly desirable since its optical transmittance is substantially constant throughout the visible spectrum and it therefore does not change the color of light passing through.

A crown can be attached to the abutment component with a wide variety of bonding agents. Examples include composites, glass ionomer cements, resin cements, zinc phosphate, zinc polycarboxylate, copolymer, and resin-modified glass ionomer cements.

In a specific embodiment, the invention provides a simplified procedure as the following: pick up an OsteoSecure abutment (commercially available from Bioinfera Inc. at Beachwood, Ohio) with the color which match the patient other tooth; place the OsteoSecure abutment on the implant, and secure with fix screw; shape the abutment to fit the occlusion relation; take impression and send to the lab; and lab technician makes the crown and send back to dentist.

In a specific embodiment, the invention provides a method for making Cerac crown as the following: pick up an OsteoSecure abutment (commercially available from Bioinfera Inc. at Beachwood, Ohio) with the color which can match the patient other tooth; place the OsteoSecure abutment on the implant, and secure with fix screw; shape the abutment to fit the occlusion relation; use Cerac machine to make a crown; and dentist put the crown on top of the abutment. An advantage of this embodiment is the direct connection with CERAC machine to make the crown without impression.

In a specific embodiment, the invention employs porcelain color spectrum (popular A-D shades such as A1-5, B1-5, C1-5) to determine the color of the crown.

In a specific embodiment, the invention provides a modifiable abutment system which includes the method, abutment, accessories and tools. This modifiable abutment system will help dentist to use the skills they already have to place the crown on top of dental implant. The technology has advantages such as reduction of the abutment inventory for dentist; elimination of the most of angle abutments; allowing a dentist to directly shape or modify the abutment without removing the abutment from the oral environment, with the modified abutment comprising a final abutment, and place Cerac crown right on top of the abutment; placing a temporary crown and a permanent crown without the use of temporary abutment in the oral environment to complete the dental restoration; better cosmetic gingival line; enabling a patient to directly pick up the color and shape by himself or herself; and cost-effectiveness on the implant crown for both doctor and dentist expenses.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for dental restoration in an oral environment comprising:
   (i) placing a sub-crown member comprising an abutment component and a dental implant component into a jawbone, wherein said abutment component and said dental implant component are two separate components and are connected and secured to each other, and wherein said abutment component comprises stainless steel, gold, silver, platinum, iron, palladium, iridium, osmium, rhodium, ruthenium; oxides; carbides such as silicon carbide; borides; nitrides; silicides; salts such as aluminosilicates, silicates such as lithium silicate, aluminates, phosphates, fluorates, zirconates, and titanates; ceramic materials such as a porcelain, a white stone containing alumina, and a glass; polymeric materials; any composites thereof such as inorganic-inorganic composites optionally bound by an organic binder, and polymeric-inorganic composites; and any combination thereof;
   (ii) directly measuring the shortest distance $X1$ between a location $L1$ on the surface of said abutment component and the surface of an object surrounding said abutment component in the oral environment;
   (iii) comparing value $X1$ with a predetermined value $Y1$, wherein $Y1>0$;
   (iv) if $X1<Y1$, directly modifying the abutment component on its location $L1$, in the oral environment, to increase said shortest distance $X1$ until $X1 \geq Y1$, in which the modifying of the abutment component is performed by a tool selected from a bur or a rotary file; diamonds; multi-use diamond dental bur; a dental carbide bur made of e.g. tungsten carbide steel; a dental sintered diamond bur; conical milling burs; a dental diamond disc; a tungsten carbide cutter; parallel milling cutter; dental steel bur; and any combinations thereof, wherein before the application of the tool, the abutment component is pretreated to weaken strength on at least location $L1$ of the abutment component; and the pretreatment is selected from vaporization, salvation or dissolution with a solvent, a chemical reaction such as etching and degradation using reagents such as HF, a base, an acid, and a complexing agent;
   (v) optionally repeating steps (ii)-(iv) on one or more of other locations $Ln$ on the surface of said abutment component with corresponding shortest distances $Xn$ and corresponding predetermined values $Yn$, wherein $Yn>0$, n is an integer, and $n \geq 2$;
   (vi) directly producing a crown based on the shape of the modified abutment component; and
   (vii) attaching the crown to the modified abutment component.

2. The method according to claim 1, in which the object surrounding said abutment component in the oral environment is selected from a periodontal tissue, a gum tissue, a tooth, and a prosthesis.

3. The method according to claim 1, in which the abutment has a hardness $H \geq 10$ K.H.N. (Knoop Hardness Number) under the ASTM D-1474 standard or a hardness equivalent thereto.

4. The method according to claim 1, in which the dental implant component comprises a material selected from the group consisting of pure titanium, titanium oxide (TiO), titanium alloy such as $TiAl_6V_4$ alloy, stainless steel, zirconium, cobalt-chromium-molybdenum alloy, polymeric material, and any combination thereof.

5. The method according to claim 1, in which the abutment component is pre-manufactured and comprises a material that is rigid, bio-compatible, and optically similar to dentin.

6. The method according to claim 1, in which the crown comprises a material selected from porcelain, metal, metal alloy, ceramic material, polymeric material, and any combination thereof.

* * * * *